United States Patent [19]
Trinks et al.

[11] Patent Number: 6,023,329
[45] Date of Patent: Feb. 8, 2000

[54] METHOD AND APPARATUS FOR DETERMINING PARAMETERS OF A GAS OR PLASMA FLOW

[76] Inventors: Ole Trinks, Zollstock 32, D - 37081 Göttingen; Walter Beck, Wakenbreite 7a, D-37079 Göttingen, both of Germany

[21] Appl. No.: 09/119,335

[22] Filed: Jul. 20, 1998

[51] Int. Cl.[7] ................................ G01J 3/30; G01B 9/02
[52] U.S. Cl. ......................... 356/311; 356/316; 356/345; 356/346
[58] Field of Search ................................ 356/311, 316, 356/300, 319, 320, 345, 346, 432, 433, 434, 435, 436, 437, 438, 442

[56] References Cited

U.S. PATENT DOCUMENTS

| | | | |
|---|---|---|---|
| 3,787,120 | 1/1974 | Hirco | 356/85 |
| 4,898,028 | 2/1990 | Brehm | 73/147 |
| 5,414,509 | 5/1995 | Veligdan | 356/349 |

*Primary Examiner*—Frank G. Font
*Assistant Examiner*—Michael P. Stafira
*Attorney, Agent, or Firm*—Thomas, Kayden, Horstemeyer & Risley

[57] ABSTRACT

A method and an apparatus determines at least one parameter of a material flow. The parameter is for example temperature, pressure or velocity of the gas or plasma flow. The material flow is either a gas or a plasma flow. The method and the apparatus are utilizing atomic absorption spectroscopy and feed a Rubidium compound into the gas or plasma flow, in which the Rubidium compound dissociates into Rubidium atoms. The Rubidium atoms are stimulated with a first laser beam and a first transmitted laser intensity is detected. First absorption lines are determined from the first transmitted laser intensity. Rubidium atoms are stimulated with a second laser beam, a second transmitted reference laser intensity is detected and second reference absorption lines are determined from the second transmitted reference laser intensity. Finally, at least one parameter of the gas or plasma flow is determined from the comparison of the first absorption lines and the second reference absorption lines of the Rubidium atoms.

23 Claims, 3 Drawing Sheets

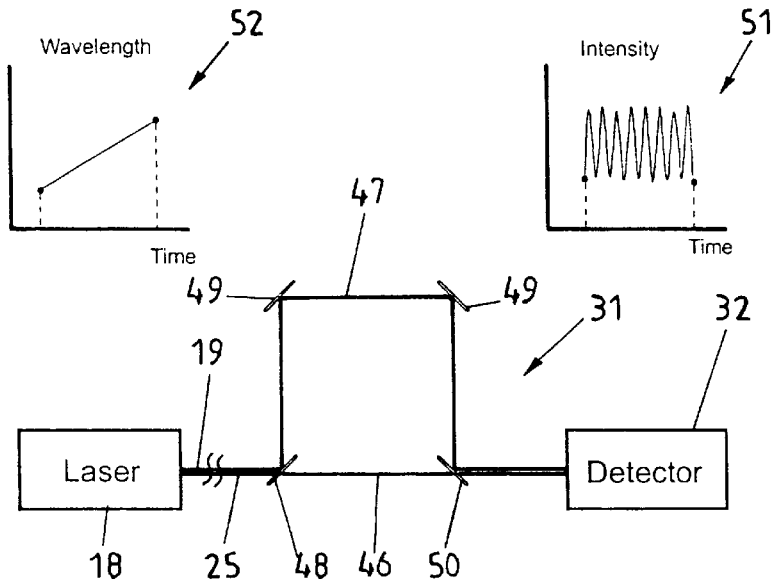
Fig. 3
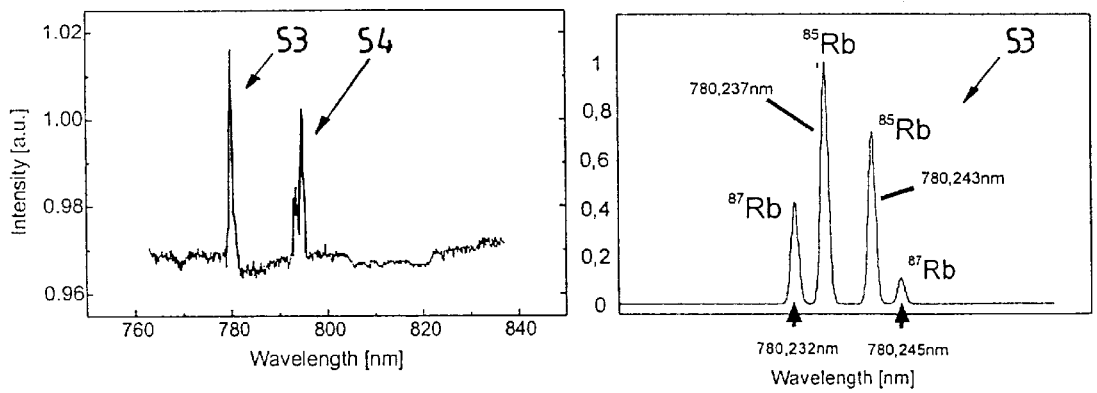
Fig. 4
Fig. 5

METHOD AND APPARATUS FOR DETERMINING PARAMETERS OF A GAS OR PLASMA FLOW

FIELD OF THE INVENTION

The invention relates to a method for determining at least one parameter, for example temperature, pressure or velocity, of a gas or plasma flow. The method is based on atomic absorption spectroscopy and is applicable to the determination of the at least one parameter of the gas or plasma flow in a high enthalpy tunnel, in a plasma jet, in gas or plasma flows of turbines, in the propulsive jet of a rocket engine and the like. Furthermore, the invention relates to an apparatus for determining at least one parameter of a gas or plasma flow.

BACKGROUND OF THE INVENTION

High enthalpy tunnels are for example used to simulate the extreme conditions which occur when a spacecraft enters the atmosphere of the earth. Because of the typically great velocity of the spacecraft, a strong pressure shock develops in front of the spacecraft. The strong pressure shock results in an impinging flow which is at least partially converted into heat. To prevent the spacecraft from burning during re-entry into the atmosphere of the earth and to keep the spacecraft maneuverable, it is very important to examine the influence of strong pressure shocks on flying bodies. In a high enthalpy tunnel, such a strong pressure shock is produced. However, the strong pressure shock in a high enthalpy tunnel only lasts for a very short period of time. Typically, after a set up period of 1 to 2 Milliseconds (ms). a stationary flow is developed within the high enthalpy tunnel. This stationary flow is the actual flow which is used for an experiment. The stationary flow only lasts up to 1 ms. Therefore, it is clear that a determination of the parameters of the flow, which is a gas flow, is quite complicated, especially, if it is intended to determine the parameters of the gas flow defined in time during the experiment period.

A method for determining at least one parameter of a gas flow, the method being based on atomic absorption spectroscopy, was first used in 1993 in the laboratory of Prof. Hanson (Stanford University) for temperature measurements behind a reflected shock in a small shock tube. To apply the method on an essentially cold flow in a high enthalpy tunnel, atoms or molecules of a specific resonance frequency and energy state need to be available in the gas or plasma flow in sufficient number.

SUMMARY OF THE INVENTION

Briefly described, the present invention comprises a method and an apparatus for determining at least one parameter of a gas or plasma flow. A plasma is defined as a at least partially ionized gas. The mixture consisting of neutral particles, ions and electrons is neutral when viewed from outside (quasi neutrality). Plasmas exist in a great variety of physical states —from the terrestrial ion sphere to a candle flame, from the glow discharge of a neon light to thermonuclear fusion plasma.

The method for determining at least one parameter of a gas or plasma flow is based on atomic absorption spectroscopy and uses the transition of Rubidium atoms. The $D_2$ resonance transition of Rubidium atoms ($5^2 S_{1/2} \rightarrow 5^2 P_{3/2}$) provides for a wavelength of shortly above 780.2 nm which is in the visible range of light, and can be stimulated with a standard laser diode. The $D_2$ resonance transition of Rubidium requires a high oscillator energy (f=0.67) so that just relatively few Rubidium atoms are necessary to have a significant absorption line in an absorption spectrum.

The $D_2$ resonance transition of Rubidium starts from the ground state of Rubidium which is always sufficiently populated. Rubidium is a metal having a relatively high vapor pressure and a low melting point. These are advantageous properties in preparing free atoms for the absorption spectroscopy in the gas flow in the high enthalpy tunnel. In the form of a Rubidium salt, particularly in the form of Rubidium nitrate ($RbNO_3$), Rubidium oxide or Rubidium chloride, for example, the Rubidium atoms can be easily fed in a test gas later forming the gas flow in the high enthalpy tunnel. The Rubidium compound will reliably dissociate under the typical conditions occurring in the high enthalpy tunnel when forming the gas flow from the test gas.

The absorption spectrum is used to determine parameters of the gas or plasma flow, such as temperature, pressure and flow velocity. The flow velocity of the gas or plasma flow is determined by observing the Doppler shift of an absorption spectrum as measured from a first laser beam being directed in a substantially non perpendicular orientation relative to a main flow direction of the gas or plasma flow. The magnitude of the Doppler shift can be determined accurately by comparison with the absorption spectrum measured in a static cell, in a reference cell or by comparison with the absorption spectrum of a second laser beam being directed in a substantially perpendicular orientation relative to a main flow direction of the gas or plasma flow.

It is therefore an object of the present invention to provide atoms of a specific resonance frequency and energy state in a gas or plasma flow suitable for atomic absorption spectroscopy.

Another object of the present invention is to provide atoms of a specific resonance frequency and energy state in a gas or plasma flow suitable for atomic absorption spectroscopy in the visible range of light.

Another object of the present invention is to provide atoms of a specific resonance frequency and energy state in a gas or plasma flow suitable for atomic absorption spectroscopy using a standard laser diode. To Another object of the present invention is to provide atoms of a specific resonance frequency and energy state in a gas or plasma flow for determining at least one parameter of the gas or plasma flow selected from the group consisting of temperature, pressure and velocity.

Other objects, features and advantages of the present invention will become apparent to one with skill in the art upon examination of the following drawings and detailed description. It is intended that all such additional objects, features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views. The drawings schematically represent an apparatus according to a preferred embodiment of the present invention, its measuring principles and illustrative data related to this embodiment.

FIG. 3 shows the principle of an interferometer used for determining the present wavelength of a diode laser of the apparatus of FIG. 2.

FIG. 4 is a Rubidium absorption spectrum in a range of 760 to 840 mm.

FIG. 5 is a Rubidium absorption peak of the Rubidium absorption spectrum according to FIG. 4 at 780.2 mm.

DETAILED DESCRIPTION OF THE INVENTION

Figure 1:
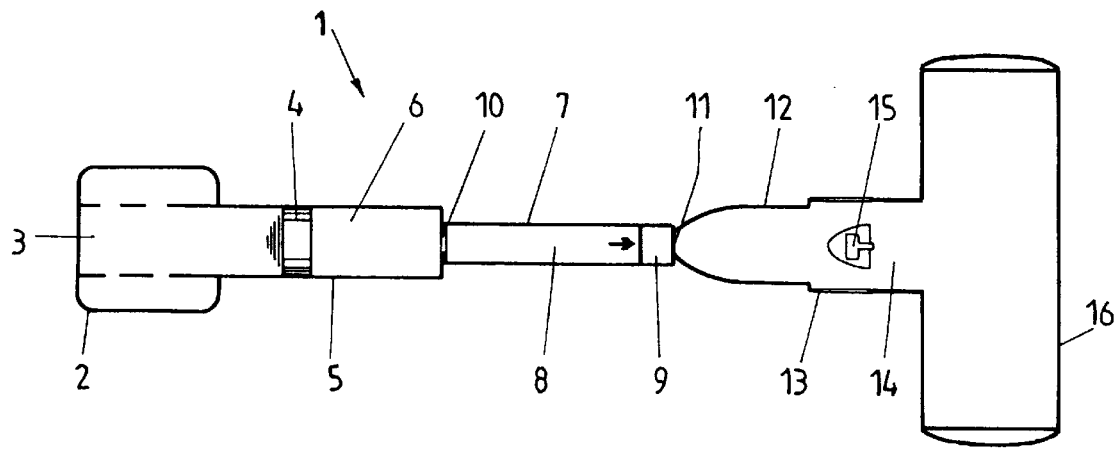
FIG. 1 schematically shows the structure of a high enthalpy tunnel.

Referring now in greater detail to the drawings, FIG. 1 illustrates a high enthalpy tunnel 1 comprising an air supply 2 for supplying compressed air 3 to accelerate a piston 4. The piston 4 is free-floating in a compression tube 5 including a driver gas 6 in front of the piston 4. The driver gas 6 is for example helium and may contain parts of argon. The piston 4 may have a weight of several hundred kg. This weight results in a high momentum of the piston 4 after being accelerated by the compressed air 3. Thus, the helium 6 in front of the piston 4 becomes highly compressed and heats up. At a predetermined burst pressure, for example 50 or 100 Mpa, a first membrane 10 closing the compression tube 5 in direction of a shock tube 7 bursts and a shock wave of the driver gas 6 enters the shock tube 7. The shock tube 7 is filled with a test gas, which may be air. From the helium 6 entering the shock tube 7 a so-called isolation shock is developed in the test gas and compresses the test gas at the front end of the shock tube 7 to a pressure of about 100 MPa with temperatures up to 10.000 K With these extreme conditions, the test gas appears in a so-called reservoir 9 at the front end of the shock tube 7. At the arrival of the shock at the front end wall of the shock tube 7 a second membrane 11 bursts. Typically, the membrane 11 is a thin plastic foil that separates the arriving isolation shock in the test gas from a prior evacuated nozzle 12 and test section 13 of the high enthalpy tunnel 1. Within nozzle, which typically has a length of several meters and is axially symmetric, the shock heated and compressed test gas 8 expands and, as a result, the test gas is accelerated up to a velocity of 6 km/s, which cools down the test gas to temperatures of 600 to 1000 K. The accelerated and cooled down test gas forms a gas or plasma flow 14. The gas or plasma flow 14 passes a model 15 to be examined which is positioned in the test section 13. The gas or plasma flow 14 then enters a dump tank 16 which is also evacuated to receive the oncoming gas or plasma flow 14 without disturbing the gas or plasma flow in the test section 13. The high enthalpy tunnel 1 may have a length of several ten meters. The high enthalpy tunnel at the DLR in Goettingen, Germany has an entire length of 60 m.

Figure 2:
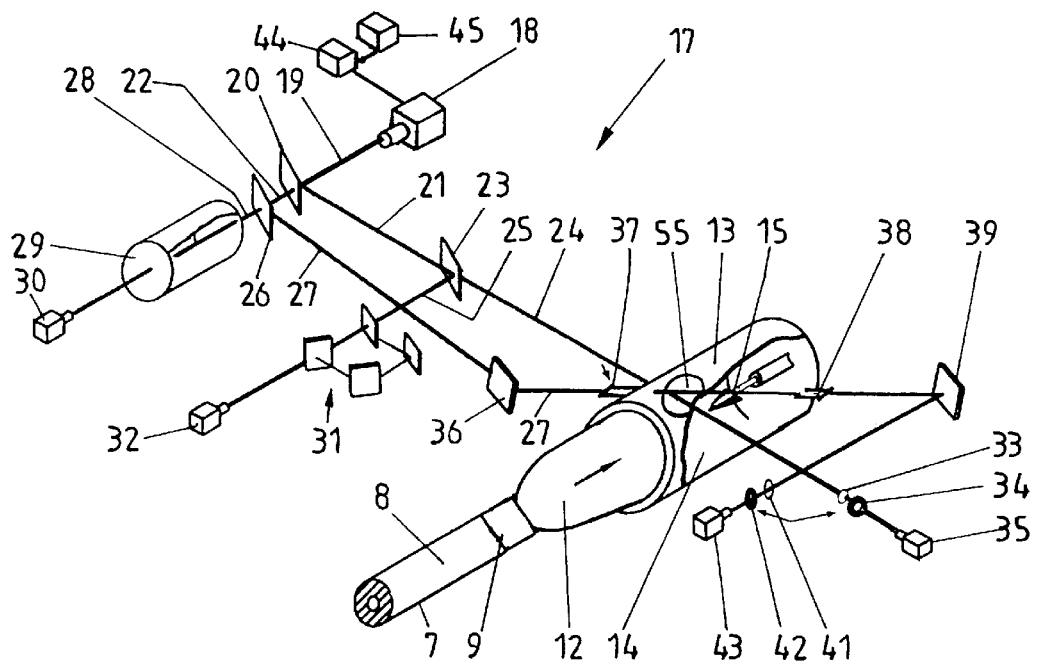
FIG. 2 shows the structure of an apparatus for atomic absorption spectroscopy in the high enthalpy tunnel of FIG. 1.

Referring now to FIG. 2, an apparatus 17 for atomic absorption spectroscopy is arranged at the test section 13 surrounding the model 15. The apparatus 17 is located downstream of the nozzle 12 and the shock tube 7 with the reservoir 9 of the high enthalpy tunnel 1 according to FIG. 1. The apparatus 17 comprises a diode laser 18 emitting laser light 19. The laser light 19 is split by a first beam splitter 20 into a first beam of laser light 21 and a second beam of laser light 22. By means of a second beam splitter 23, the first beam of laser light 21 is further split into a third beam of laser light 24 and a fourth beam of laser light 25. The second beam of laser light 22 is further split by third beam splitter 26 into a fifth beam of laser light 27 and a sixth beam of laser light 28. The sixth beam of laser light 28 enters a reference cell 29 containing Rubidium atoms at defined pressure and temperature. A photo detector 30 measures the intensity of the sixth beam of laser light 28 passing through the reference cell 29. The fourth beam of laser light 25 enters an interferometer 31 with a photo detector 32 which will be explained more detailed with reference to FIG. 3. The third beam of laser light 24 crosses the test section 13 and the gas or plasma flow 14 at right angles. The beam of laser light 24 enters the test section 13 and re-exits from the test section through windows 55. The part of the laser light 24 passing through the test section 13 is collimated by a lens 33 and an aperture 34 in front of a photo detector 35 detecting the intensity of the beam of laser light 24 passing through the test section 13. The beam of laser light 27 is deflected by a mirror 36 so that it enters the test section 13 through a window 37 which is oriented under an angle of approximately 53° with regard to the main direction of the flow 14 and the main extension direction of the test section 13. The beam of laser light 27 re-exits the test section through a further 53°-window 38. Then it is deflected by a mirror 39 through a collimating arrangement of a lens 40 and an aperture 42 on a photo detector 43. The diode laser 18 is controlled by a laser controller 44 which controls the injection-current of the diode of the diode laser 18. The laser controller 44 receives a control function from a function generator 45. The control function from function generator 45 is a triangular function directly resulting in a sweeping up and down of the intensity of the laser light 19 emitted by the diode laser 18. With the sweeping of the intensity of the diode laser 18, however, the wavelength of the diode laser 18 is also swept up and down. This allows to scan an absorption line in the absorption spectrum of the Rubidium atoms in the reference cell 29, and of the Rubidium atoms fed into the flow 14 in the test section 13 with the diode laser 18. The present wavelength of the laser light emitted from the diode laser 18 is determined by means of the interferometer 31. The standard absorption spectrum of Rubidium atoms is obtained by means of the reference cell 29 and the photo detector 30. The absorption spectrum of the Rubidium atoms fed into the flow 14 in the test section 13, which is detected by the photo detectors 35 and 43 at different angles with regard to the main direction of the gas or plasma flow 14 allows determining different parameters of the gas or plasma flow 14. Although the gas or plasma flow 14 only keeps the desired test conditions for a period of time up to I ms, the apparatus 17 according to FIG. 2 may also determine the parameters of the gas or plasma flow 14 defined in time during the test period as the function generator 45 may create its triangular function with a frequency of about 1 MHz which corresponds to about 2000 single measuring periods (up and down) during a test period of 1 ms. The absorption of the beam of laser light 24 by Rubidium atoms in the flow 14 is essentially not affected by the velocity of the flow 14 as the beam of laser light 24 crosses the gas or plasma flow 14 perpendicularly. Thus, the absorption spectrum obtained by the photo detector 35 mainly includes information about the temperature of the gas or plasma flow 14. The information about the temperature is contained in the peak width of the scanned absorption lines of the Rubidium atoms. The absolute peak height indicates a partial pressure of the Rubidium atoms in the gas or plasma flow 14 as long as the Rubidium atoms are distributed homogeneously. This homogenous distribution of the Rubidium atoms in the gas or plasma flow 14 is achieved if, for example, an aqueous Rubidium nitrate solution is applied to the wall at the front end of the shock tube 7, i.e. in the reservoir 9, and by letting the aqueous solution dry. Under the conditions of the isolation shock created in the test gas 8 in the shock tube 7, the remaining Rubidium salt dissociates into atomic Rubidium. The beam of laser light 27 is affected by the velocity of the gas or plasma flow 14 as it is extending through the test section 13 partially in the direction of the gas or plasma flow 14. Concretely, the absorption spectrum of the Rubidium atoms detected with the photo detector 43 is Doppler shifted with regard to the absorption spectrum of Rubidium atoms in a non-moving gas, for example as provided in the reference cell 29.

FIG. 3 shows the structure of the interferometer 31 with the detector 32 according to FIG. 2, for determining the present wavelength of the laser light 19 emitted from the diode laser 18. The beam of laser light 25 entering the interferometer is split into two parts 46 and 47 by a beam splitter 48. While the part 46 of the beam of laser light 25 shows a straight optical path to the detector 32, part 47 has an extended optical path between a beam splitter 48, mirrors 49 and a further beam splitter 50. By means of a beam splitter 50, the parts 46 and 47 of the beam of laser light 25 are superposed. Due to the different length of the optical paths of the parts 46 and 47, the superposition shows an intensity 51 varying with the wavelength 52 of the laser light 19 emitted by the diode laser 18. When the wavelength increases linearly, the intensity shows a sine-shaped curve. In case of the diode laser according to FIG. 2 the change of wavelength of the emitted laser light 19 is superposed with a intensity variation. Of course, this intensity variation is also found superposed to the sine of the intensity due to the changing wavelength. However, this is not shown in FIG. 3. The interferometer 31 allows determining the relative wavelength of the laser light 19 emitted by the laser 18. The reference cell 29 according to FIG. 2 allows the absolute determination of special wavelengths as they match with known absorption lines in the absorption spectrum of the Rubidium atoms contained in the reference cell 29.

FIG. 4 shows an absorption spectrum of atomic Rubidium measured over a range of wavelengths of nearly 760 to 840 nm. This absorption spectrum shows two peaks 53 and 54. The peak 53 is in the area of a wavelength of 780 nm. The peak 54 is in the area of about 796 nm. Here, only peak 53 is used.

Figure 6:
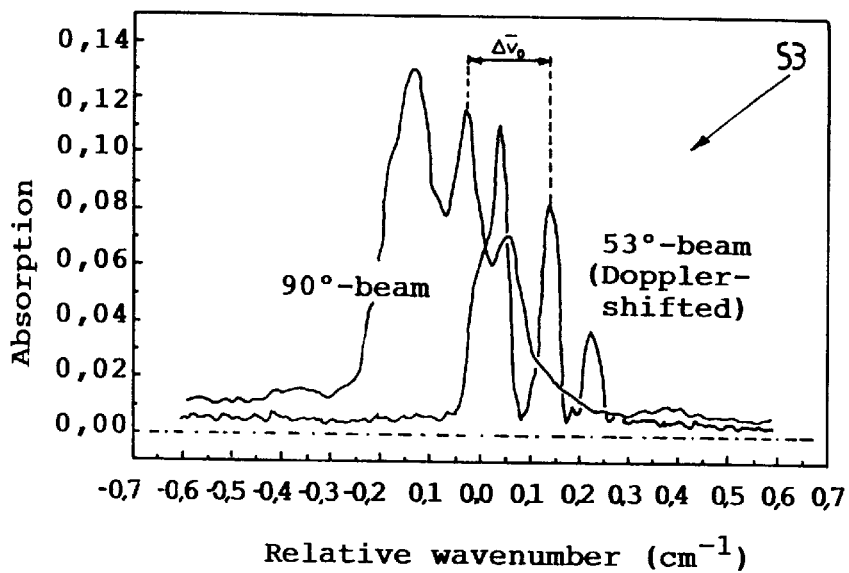
FIG. 6 shows a Doppler-shift of the Rubidium absorption peak according to FIG. 5 occurring in absorption measurement with the apparatus according to FIG. 2.

FIG. 5 only shows peak 53 of the absorption spectrum of Rubidium as obtained by means of the reference cell 29 and the photo detector 30 according to FIG. 2. The bandwidth of the diode laser 18 is so narrow that the resolution of peak 53 in FIG. 5 resolves the hyperfine structure of the peak 53 and an effect of different Rubidium isotopes 85Rb and 87Rb. FIG. 6 shows the same peak 53 as detected by the detectors 35 and 43 according to FIG. 2. The peak 53 as detected by the photo detector 35 is the 90°-beam. All lines of the peak are broadened due to a temperature effect. The temperature can directly be determined from the width of the whole peak 53 or any line of peak 53, if separable. The 53°-beam corresponds to the photo detector 43 and shows a Doppler-shift to the right, i.e. to higher frequencies, as the frequency of the beam of laser light 27 has to compensate for the velocity of gas or plasma flow 14 flowing in the same direction. The Doppler-shift is directly related to the velocity of the Rubidium atoms. The Doppler shifted peak 53 is less broad than the non-shifted peak 53 not because the 53°-beam is not depending on the temperature of the absorbing Rubidium atoms. Instead, the windows 37 and 38 according to FIG. 2 comprise light guides (not shown in FIG. 2) which reduce the area covered by the free beam of laser light 27 within the test section of the core region of the gas or plasma flow 14, and it is known that in the core region, the gas or plasma flow 14 in a high enthalpy tunnel has a temperature less than in the region surrounding the core. Such light guides can always be used to reduce the area covered by the free beams of laser light crossing the test section for concentrating the measurement of the respective parameter of interest to the area.

Figure 7:
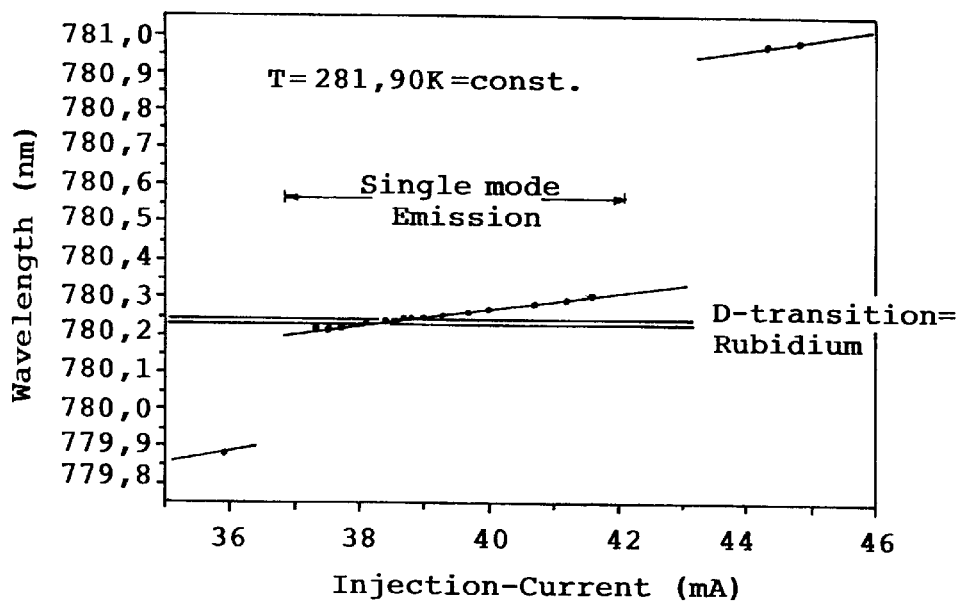
FIG. 7 shows the dependency of the wavelength of a laser fight emitted from the diode laser of the apparatus according to FIG. 2 on the injection-current of the diode with regard to the $D_2$ transition of Rubidium.

FIG. 7 shows details of the wavelength of the laser light 19 emitted by the laser 18 according to FIG. 2. The wavelength is plotted versus the injection-current of the diode laser. In the region of the $D_2$ transition of Rubidium, the diode laser 18 emits in single mode and there is a very good linear correlation between the wavelength and the injection-current. Despite its ideal properties, the laser diode 18 can be a very inexpensive mass-produced product. In the preferred embodiment of the invention, the laser diode 18 is a GaAlAs-laser diode of the type RHOM RLD-78 NP. This diode type emits in single mode at room temperature with a wavelength of 780 nm. The optical output power lies near 5 mW.

Many variations and modifications may be made to the preferred embodiment of the invention without departing substantially from the spirit and principles of the invention. All such modifications and variations are intended to be included herein within the scope of the present invention, as defined by the following claims.

We claim:

1. A method for determining at least one parameter of a gas or plasma flow, said method being based on atomic absorption spectroscopy, said method comprising the steps of:

feeding a Rubidium compound into the gas or plasma flow, in which the Rubidium compound dissociates into Rubidium atoms;

stimulating the Rubidium atoms with a first laser beam;

detecting a first transmitted laser intensity;

determining first absorption lines from the first transmitted laser intensity;

stimulating Rubidium atoms with a second laser beam;

detecting a second transmitted reference laser intensity;

determining second reference absorption lines from the second transmitted reference laser intensity; and determining at least one parameter of the gas or plasma flow from the comparison of the first absorption lines and the second reference absorption lines of the Rubidium atoms.

2. The method of claim 1, further comprising the step of: feeding a Rubidium compound into a reference cell containing a gas or plasma of defined pressure and temperature in which the Rubidium compound dissociates into Rubidium atoms prior to said step of stimulating the Rubidium atoms with a first laser beam.

3. The method of claim 1, wherein the Rubidium atoms are stimulated with the second laser beam in a substantially perpendicular orientation relative to a main flow direction of the Rubidium atoms.

4. The method of claim 1, wherein the Rubidium compound comprises a salt.

5. The method of claim 1, wherein the Rubidium compound comprises Rubidium nitrate.

6. The method of claim 1, wherein the step of stimulating the Rubidium atoms with a first laser beam is accomplished by directing the laser beam toward the Rubidium atoms in a substantially perpendicular orientation relative to a main flow direction of the Rubidium atoms.

7. The method of claim 1, wherein one parameter is temperature.

8. The method of claim 1, wherein one parameter is pressure.

9. The method of claim 1, wherein the steps of stimulating the Rubidium atoms with the first and second laser beam are accomplished by sweeping the laser to scan a relevant frequency range of approximately 780.15 nm to 780.35 nm including a $D_2$ resonant transition of Rubidium atoms at a wavelength of 780.2 nm.

10. A method for determining flow velocity of a gas or plasma flow, said method being based on atomic absorption spectroscopy, said method comprising the steps of:

feeding a Rubidium compound into the gas or plasma flow, in which the Rubidium compound dissociates into Rubidium atoms;

directing a first laser beam of a diode laser toward the Rubidium atoms such that the first laser beam is directed in a substantially perpendicular orientation relative to a main flow direction of the Rubidium atoms;

stimulating the Rubidium atoms with the first laser beam in a frequency range including a $D_2$ resonant transition of Rubidium atoms at a wavelength of approximately 780.2 nm;

detecting a first transmitted laser intensity;

determining a first absorption line from the first transmitted laser intensity;

directing a second laser beam of a diode laser toward the Rubidium atoms such that the second laser beam is directed in a non perpendicular orientation relative to the main flow direction of the Rubidium atoms;

stimulating the Rubidium atoms with the second laser beam in a frequency range including the $D_2$ resonant transition of Rubidium atoms at a wavelength of approximately 780.2 nm;

detecting a second transmitted laser intensity;

determining a second absorption line from the second transmitted laser intensity;

acquiring a Doppler shifted and broadened absorption line of the first and second transmitted laser intensities;

feeding a Rubidium compound into a reference cell containing a gas or plasma of defined velocity, in which the Rubidium compound dissociates into Rubidium atoms;

stimulating the Rubidium atoms with a third laser beam;

detecting the third transmitted laser intensity;

determining the third absorption line from the third transmitted laser intensity; and determining flow velocity of the gas or plasma flow from the shift in the acquired Doppler shifted and broadened first and second absorption line with respect to the third absorption line of the Rubidium atoms, wherein the magnitude of the shift is directly proportional to the flow velocity of the gas or plasma flow.

11. The method of claim 10, wherein the laser beam directed in a non perpendicular orientation is directed toward the main flow direction of the Rubidium atoms at an angle of approximately between 40 and 60 degrees.

12. An apparatus for determining at least one parameter of a gas or plasma flow, comprising:

at least one laser for stimulating Rubidium atoms flowing in a main flow direction of the gas or plasma flow with a first laser beam in a frequency range including a $D_2$ resonant transition of Rubidium atoms at a wavelength of approximately 780.2 nm;

at least one photo detector detecting a first transmitted laser intensity of said laser for stimulating Rubidium atoms; wherein a first absorption line is determined from the first transmitted laser intensity;

a reference cell containing Rubidium atoms in a gas or plasma having defined pressure and temperature;

a second laser beam for stimulating Rubidium atoms in said reference cell in a frequency range including the $D_2$ resonant transition of Rubidium atoms at a wavelength of approximately 780.2 nm;

at least one photo detector detecting a second transmitted laser intensity of the second laser beam; wherein a second absorption line is determined from the second transmitted laser intensity, and wherein at least one parameter of the gas or plasma flow is determined from the comparison of the first and the second absorption line.

13. The apparatus of claim 12, wherein said at least one laser is a diode laser.

14. The apparatus of claim 12, wherein the at least one laser is directed toward the Rubidium atoms such that at least one laser beam emitted from said laser would project in a direction that is substantially perpendicular to the main flow direction of the Rubidium atoms.

15. The apparatus of claim 12, wherein one parameter is temperature.

16. The apparatus of claim 12, wherein one parameter is pressure.

17. An apparatus for determining flow velocity of a gas or plasma flow, comprising:

a high enthalpy tunnel;

at least one laser for stimulating Rubidium atoms flowing in a main flow direction of the gas or plasma flow with a first laser beam in a frequency range including a $D_2$ resonant transition of Rubidium atoms at a wavelength of approximately 780.2 nm; the first laser beam being directed in a perpendicular orientation relative to the main flow direction of the Rubidium atoms;

at least one photo detector detecting a first transmitted laser intensity of the first laser beam; wherein a first absorption line is determined from the first transmitted laser intensity;

a second laser beam stimulating Rubidium atoms flowing in the main flow direction of the gas or plasma flow in a frequency range including the $D_2$ resonant transition of Rubidium atoms at a wavelength of approximately 780.2 nm, the second laser beam being directed in a non perpendicular orientation relative to the main flow direction of the Rubidium atoms;

at least one photo detector detecting a transmitted laser intensity of the second laser beam stimulating Rubidium atoms in said high enthalpy tunnel; wherein a second absorption line is determined from the second transmitted laser intensity wherein a Doppler shifted and broadened absorption line of the first and second transmitted laser intensity is acquired;

a reference cell containing Rubidium atoms in a gas or plasma having a defined velocity;

a third laser beam stimulating Rubidium atoms in said reference cell in a frequency range including the $D_2$ resonant transition of Rubidium atoms at a wavelength of approximately 780.2 nm;

at least one photo detector detecting a third transmitted laser intensity of the third laser beam for stimulating Rubidium atoms in said reference cell; wherein a third absorption line is determined from the third transmitted laser intensity, wherein the flow velocity of the gas or plasma flow is determined from the shift in the acquired Doppler shifted and broadened first and second absorption line with respect to the third absorption line of the Rubidium atoms in the reference cell, wherein the magnitude of the shift is directly proportional to the flow velocity of the gas or plasma flow.

18. An apparatus for determining the flow velocity of a gas or plasma flow, comprising:

means for feeding a Rubidium compound into the gas or plasma flow, in which the Rubidium compound dissociates into Rubidium atoms;

means for stimulating the Rubidium atoms with a laser beam;

means for detecting a transmitted laser intensity;

means for determining absorption lines from the transmitted laser intensity means for stimulating the Rubidium atoms with a reference laser beam;

means for detecting a transmitted reference laser intensity;

means for determining reference absorption lines from the transmitted reference laser intensity; and means for determining at least one parameter of the gas or plasma flow from the comparison of the absorption lines and the reference absorption lines of the Rubidium atoms.

19. The apparatus of claim 18, wherein said means for stimulating the Rubidium atoms with the reference laser beam comprise a reference cell containing a gas of defined pressure and temperature into which a Rubidium compound is fed and in which the Rubidium compound dissociates into Rubidium atoms.

20. The apparatus of claim 18, wherein the means for stimulating the Rubidium atoms with a reference laser beam stimulate the Rubidium atoms in a substantially perpendicular orientation relative to a main flow direction of the Rubidium atoms.

21. The apparatus of claim 18, wherein the Rubidium compound comprises a salt.

22. The apparatus of claim 18, wherein the Rubidium compound comprises Rubidium nitrate.

23. The apparatus of claim 18, wherein the means for stimulating the Rubidium atoms sweep for scanning a relevant frequency range of approximately 780.15 nm to 780.35 nm including the $D_2$ resonant transition of Rubidium atoms at a wavelength of approximately 780.2 nm.

* * * * *